(12) United States Patent
Brott et al.

(10) Patent No.: US 7,193,037 B2
(45) Date of Patent: Mar. 20, 2007

(54) METHOD AND APPARATUS FOR USE OF THERMALLY SWITCHING PROTEINS IN SENSING AND DETECTING DEVICES

(75) Inventors: Lawrence L. Brott, West Chester, OH (US); Rajesh R. Naik, Dayton, OH (US); Morley O. Stone, Bellbrook, OH (US); Daniel C. Carter, Huntsville, AL (US)

(73) Assignees: The United States of America as represented by the Secretary of the Air Force, Washington, DC (US); New Century Pharmaceuticals, Inc., Huntsville, AL (US)

( * ) Notice: Subject to any disclaimer, the term of this patent is extended or adjusted under 35 U.S.C. 154(b) by 286 days.

(21) Appl. No.: 10/313,010

(22) Filed: Dec. 6, 2002

(65) Prior Publication Data
US 2007/0037133 A1    Feb. 15, 2007

Related U.S. Application Data

(60) Provisional application No. 60/391,089, filed on Jun. 25, 2002, provisional application No. 60/336,145, filed on Dec. 6, 2001.

(51) Int. Cl.
*A61K 38/00* (2006.01)
(52) U.S. Cl. .................... 530/324; 530/350; 435/288.7
(58) Field of Classification Search .................... 435/4, 435/283.1, 285.2, 287.1
See application file for complete search history.

(56) References Cited

U.S. PATENT DOCUMENTS 6,160,257 A    12/2000    Deb

OTHER PUBLICATIONS

Storz, Gisela; An RNA Thermometer, vol. 13(6), pp. 633-636, (Mar. 1999).*
Beamline 12: Circular Dichroism, Research Article. pp. 111-113, (1999).*
Naik, R. et al, "Biosensors & Bioelectronics", vol. 16 (Issues 9-12), pp. 1051-1057, (Dec. 2001).*
Naik et al., "The thermostability of an alpha-helical coiled-coil protein and its potential use in sensor applications", Biosensors & Bioelectronics, 2001, vol. 16, pp. 1051-1057, Abstract.
Hurme, "Temperature sensing in bacterial gene regulation—what it all boils down to", Molec. Microbiol., 1998, vol. 30, No. 1, pp. 1-6.
Koski et al., "A new alpha-helical coiled coil protein encoded by the *Salmonella typhirium* viulencfe plasmid", J. Biol. Chem. 1992, vol. 267, No. 17, pp. 12258-12265, Abstract.

* cited by examiner

*Primary Examiner*—Ralph Gitomer
(74) *Attorney, Agent, or Firm*—B. Aaron Schulman; Stites & Harbison PLLC

(57) ABSTRACT

An apparatus and method for detecting infrared radiation is provided which comprises a temperature-sensing helical coiled-coil protein such as TlpA, CC1, collagen or myosin, incorporated into an electrically conductive film or gel deposited onto an electrically conductive medium such as an electrode, means for recording changes in conductivity or resistance of the conductive film or gel caused by the presence of infrared radiation and the effect of the infrared radiation on the thermal-sensing protein, and means to analyze the changes in conductivity or resistance in the conductive film caused by the infrared radiation so as to determine if infrared radiation is present. By virtue of the present invention, a "biomimetic" infrared sensor is provided which can integrate a recombinantly produced thermally sensitive protein in a conductive polymer matrix, such as a film or gel, so as to provide for the first time a low-cost, lightweight, conformable, and even possibly disposable, infrared detecting device having high sensitivity and excellent dynamic range.

6 Claims, 8 Drawing Sheets

THEORY

At low temperatures:
- Polymer and biomolecule tightly bind the carbon black in place

At higher temperatures:
- Polymer and biomolecule expand, thereby allowing the carbon black to rearrange and agglomerate
- Conductivity increases

| 256 | | | | 260 | | | | | | | 270 |
|---|---|---|---|---|---|---|---|---|---|---|---|
| Thr | Arg | Glu | Thr | Leu | Gln | Gln | Arg | Leu | Glu | Gln | Ala | Ile | Ala |

| 271 | | | | 275 | | | | | 280 | | |
|---|---|---|---|---|---|---|---|---|---|---|---|
| Asp | Thr | Gln | Ala | Arg | Ala | Gly | Glu | Ile | Ala | Leu | Glu | Arg | Asp |

| 285 | | | | | 290 | | | | | | |
|---|---|---|---|---|---|---|---|---|---|---|---|
| Arg | Val | Ser | Ser | Leu | Thr | Ala | Arg | Leu | Glu | Ser | Gln | Glu | Lys |

299
Ala

FIGURE 8

METHOD AND APPARATUS FOR USE OF THERMALLY SWITCHING PROTEINS IN SENSING AND DETECTING DEVICES

CROSS-REFERENCE TO RELATED APPLICATIONS

This application claims the benefit of U.S. Provisional Application Ser. No. 60/391,089, filed Jun. 25, 2002, and of U.S. Provisional Application Ser. No. 60/336,145, filed Dec. 6, 2001.

STATEMENT OF GOVERNMENTAL INTEREST

This invention was made in the performance of a Cooperative Research and Development Agreement with the Department of the Air Force. The Government of the United States has certain rights to use the invention.

FIELD OF THE INVENTION

This invention relates in general to a method for utilizing thermally switching proteins in devices which can sense and detect changes in temperature and thus be used in a variety of sensing systems, and more particularly to a method and apparatus for utilizing helical coiled-coil proteins which undergo a conformational change at particular temperatures, such as the thermal switching protein TlpA and the modified protein TlpA8, in conductive polymeric matrices in order to obtain efficient and inexpensive, but still highly sensitive, temperature and infrared monitoring detection devices which can be useful in a broad array of applications calling for IR detection.

BACKGROUND OF THE INVENTION

Infrared sensing devices are well known and are now utilized in a wide variety of applications including night vision devices, enhanced aviation vision systems, fire detection, surveillance and security, search and rescue devices, and even medical imaging and diagnostics. Current state-of-the-art devices in this field include bolometers which are composed of semiconductors using vanadium oxide as the active component. These devices can provide effective room temperature infrared detection with a sensitivity in the 8–15 micron range. Devices currently on the market that deal with infrared detection technology include the Spectrum/RM of Texas Infrared Inc., the Thermacam® from FLIR Systems, and the PalmIR PRO from Raytheon. Still other devices in this field include those which utilize PtSi and measure infrared radiation by means of changes in capacitance, and those which utilize PbSe and InSb which are photoconductive detectors which operate at room temperature with about a 20% change in response per degree Centigrade.

Unfortunately, the great limitation on the potential usefulness and applicability of current infrared devices is their great expense. Currently, cameras in this field such as the ones described above have costs in the tens of thousands of dollars, and prices typically range from about $10,000 to $50,000 depending on range and detection sensitivity. It is clear that there exists a distinct need to provide technology by which a low-cost system of infrared detection can be obtained so that the potential benefits of infrared detection, such as medical imaging and search and rescue devices, can become affordable and thus more commonly available so that the public can benefit from such devices. It is also clear that there exists a need for providing improved hybrid organic/inorganic nanostructures utilizing photo polymerization which can allow for enhanced optical reflectivity and the creation of holographic or other optical gratings which can be used to form a broad array of biosensors and other sensing devices.

Previously, it has been recognized in nature that certain proteins apparently are configured to have conformational shapes which allow a particular function when one set of conditions is present, yet another shape under different conditions or stimuli which provides for a different function. An example of this conformationally changing shape is the "coiled-coil" type of protein which confers a variety of functional capabilities, including enabling proteins such as myosin to function in the contractile apparatus associated with muscle cells and associated non-muscle structures. One such conformationally changing protein appears to be the TlpA protein encoded by the virulence plasmid of *Salmonella* bacteria which is an α-helical protein that forms an elongated coiled-coil homodimer. A number of studies regarding this protein appear to show that it operates in the bacteria as a temperature-sensing gene regulator. However, it has never been disclosed or suggested that this protein, or active fragments therefrom, could be utilized in devices which could monitor and detect heat in the form of infrared radiation. There is thus a distinct need in the field to develop devices which can make use of the thermal conformation shifts in proteins such as TlpA and its active fragments so as to detect infrared radiation.

SUMMARY OF THE INVENTION

Accordingly, it is thus an object of the present invention to create devices which can detect infrared radiation which are efficient yet inexpensive, and which thus can be used in a variety of applications.

It is further an object of the present invention to provide an apparatus which can utilize a conformational change protein and translate a change in temperature into electrical conductance and thus be able to detect heat or infrared radiation.

It is still further an object of the present invention to develop proteins and protein fragments which are capable of achieving reversible conformational changes so as to be useful in devices which utilize such conformational changes to detect heat and/or infrared radiation.

It is even further an object of the present invention to provide methods of detecting infrared radiation using conductive polymeric matrices that contain proteins which possess the ability to reversibly change conformation depending on thermal characteristics.

It is yet a further object of the present invention to provide hybrid organic/inorganic nanostructures with improved optical reflectivity to create holographic or other optical gratings which may be utilized in the infrared detectors of the invention, and which can be integrated with the coiled-coil proteins of the present invention to form a broad array of biosensors.

It is still further an object of the invention to develop infrared sensing devices that reduce costs of manufacturing by several orders of magnitude from currently available devices, that are easy to manufacture and utilize readily available materials, that reduce and potentially eliminates all cooling requirements such as are required in many highly sensitive IR detectors, that are extremely lightweight and can be made disposable, if necessary, and which have excellent dynamic range and high sensitivity thresholds.

These and other objects are achieved by virtue of the present invention which provides a method and apparatus for sensing infrared radiation comprising a helical temperature-sensing coiled-coil (CC) protein such as TlpA, collagen or myosin contained in an electrically conductive film or gel deposited onto an electrically conductive medium such as an electrode, means for recording changes in conductivity or resistance of the conductive film or gel caused by the presence of infrared radiation and the effect of the infrared radiation on the CC protein, and means to analyze the changes in conductivity or resistance in the conductive film caused by the infrared radiation so as to determine if infrared radiation is present.

These and other features of the present invention as set forth in, or will become obvious from, the detailed description of the preferred embodiments provided hereinbelow.

BRIEF DESCRIPTION OF THE DRAWING FIGURES

FIG. 8 shows the amino acid sequence (SEQ ID NO:!) of the TlpA8 protein of the present invention.

DETAILED DESCRIPTION OF THE PREFERRED EMBODIMENTS

Figure 1:
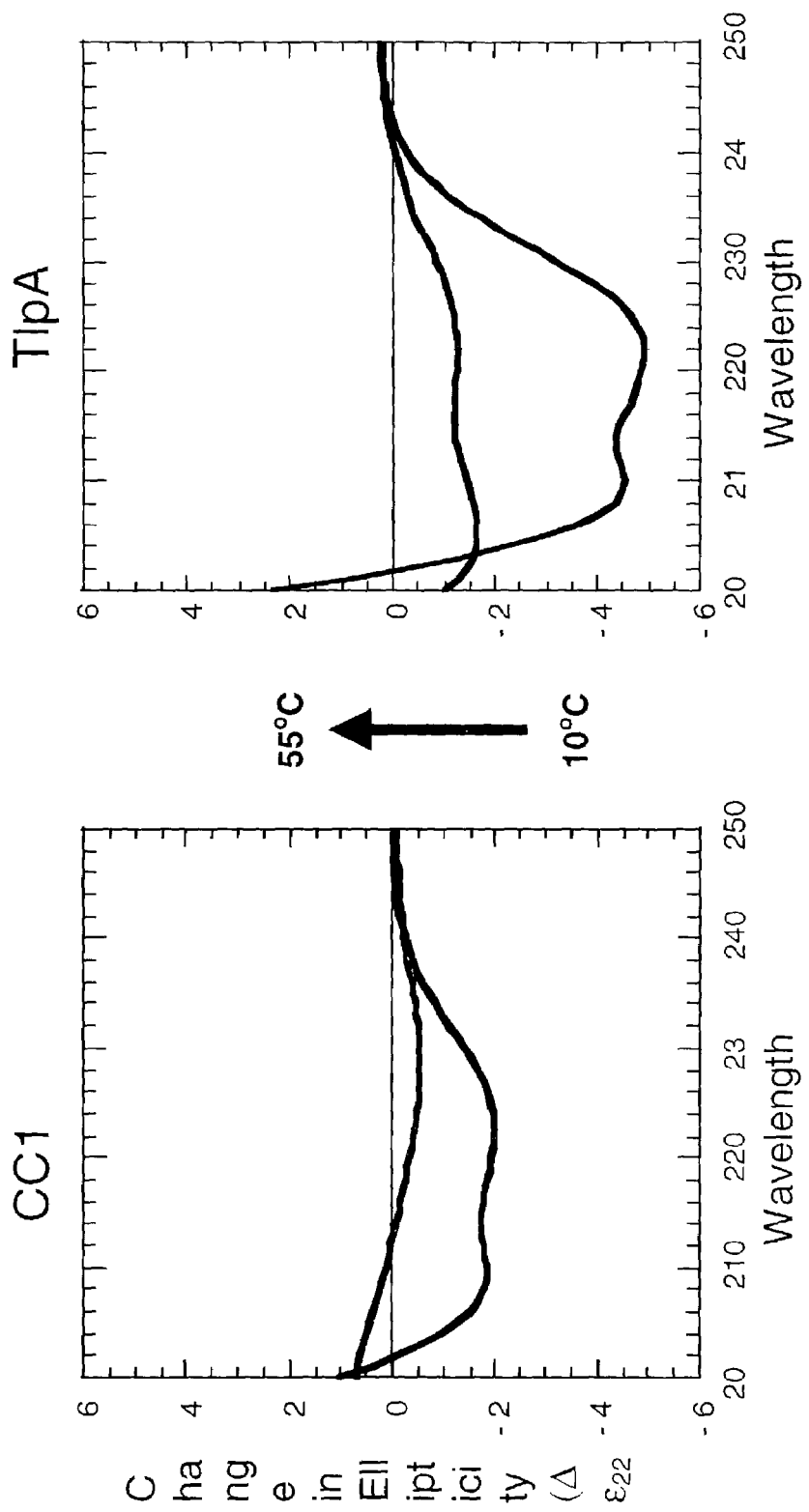
FIG. 1 is a graphic representation of changes in ellipticity of thermal sensing proteins in accordance with the invention at different temperatures.

In accordance with the present invention, there is provided an apparatus for detecting infrared radiation in a variety of sensing systems which comprises the use of conformationally changing proteins embedded in a conductive polymer matrix. In a preferred embodiment, these conformationally changing proteins comprise any protein capable of significant and reversible conformational change induced by temperature changes within a range of −15° C. to 60° C., and include proteins such as albumin, as well as oligomeric proteins or fragments capable of such a reversible conformational change induced by temperature. In addition, these types of conformationally changing proteins in accordance with the invention include helical coiled-coil (CC) proteins capable of reversible conformational change induced by temperature changes within a range of −15° C. to 60° C. By helical coiled-coil protein is meant any protein or peptide which undergoes reversible temperature-dependent conformational changes and thus include those protein fragments from the coiled-coil proteins or derivatives therefrom which maintain the conformational change of the full coiled-coil protein. These coiled-coil proteins include TlpA, CC1, collagen and myosin which all have similar switching mechanism, and in the description as follows, the invention is described in terms of the TlpA protein specifically, although any of the other coiled-coil proteins with the properties described above can be utilized in the invention.

In accordance with the present invention, use is made of the helical coiled coil TlpA protein, such as the thermal switching TlpA protein of the type found in *Salmonella* bacteria, or active fragments thereof which maintain the ability to undergo the conformational change which is dependent upon a change of temperature. Accordingly, by "TlpA protein" is meant those proteins which undergo the type of conformational change observed in the TlpA protein such as expressed in *Salmonella* bacteria, such as *Salmonella typhimurium* (1), including those protein fragments isolated from the TlpA protein, such as TlpA8 as described further below, or derivatives which maintain the conformational change of the full TlpA protein, or even further proteins with a similar switching pattern. In accordance with the invention, as described in detail further below, the preferred apparatus includes the incorporation of the TlpA protein or its active fragments into a conductive polymer matrix so as to be useful in a variety of sensing systems that utilize detection of infrared radiation. By virtue of the present invention, a "biomimetic" infrared sensor is provided which can integrate a recombinantly produced thermally sensitive TlpA protein in a conductive polymer matrix, such as a film or gel, so as to provide for the first time a low-cost, lightweight, conformable, and even possibly disposable, infrared detecting device having high sensitivity and excellent dynamic range.

In the current field of infrared detection, there are infrared sensing elements which are sensitive to radiation in the wavelength range from 1 to 15 microns and have numerous commercial and government applications (including military and law enforcement agencies). These applications include, but are not limited to night vision devices, military weapons targeting, aircraft enhanced vision systems, surveillance/security, fire fighting, fire detection, search and rescue devices, devices for predictive maintenance, process control, research and development, driver's vision enhancers and medical imaging and diagnostics. These highly sensitive detection systems are generally used in three temperature dependent formats depending on the sensitivity required by the application, namely room temperature, cryogenic and near room temperature cooled detectors. Public available information indicates that the current market for these technologies in the U.S. is approximately $1 Billion and growing at a rate of 7% per annum. The markets are currently limited by the great expense of highly sensitive imaging systems (usually from 10 to 50K each). Accordingly, the present invention is designed to provide a much cheaper alternative to these expensive infrared detection devices, and thus allow the benefits of infrared detection devices to be more accessible to the public.

In the animal kingdom, there have been examples of thermal or heat detection systems occurring in nature, but prior to the present invention, no such systems have been usable in creating infrared detection systems that could be used in commercial products. For example, it has been known that certain snakes, such as the python and other venomous snakes, apparently possess infrared sensing structures which are used for close range detection only of heat. However, this system appears to be based on complicated proteins in the snakes' pit organs which are difficult to produce using recombinant methods (2). The present invention utilizes helical coiled coil proteins such as the TlpA protein which has been shown to be connected to heat detection in bacteria. In many bacteria, there exist such heat sensitive molecular switches, such as those involved in heat sensing reactions and the expression of shock proteins. In bacteria, the thermal sensing TlpA protein has been isolated and now can be produced by recombinant methods and expressed so as to be useful in the present invention. FIG. 1 illustrates the optical dispersion plot of two bacterial thermal sensing proteins, including the TlpA protein of the invention, versus temperature. In other studies, the thermal switch properties of the TlpA protein were observed (3). Subsequently, a modified protein with greater stability, smaller size and enhanced solubility characteristics, TlpA8, was successfully produced and incorporated into the infrared devices in accordance with the present invention as described in more detail below.

Figure 2:
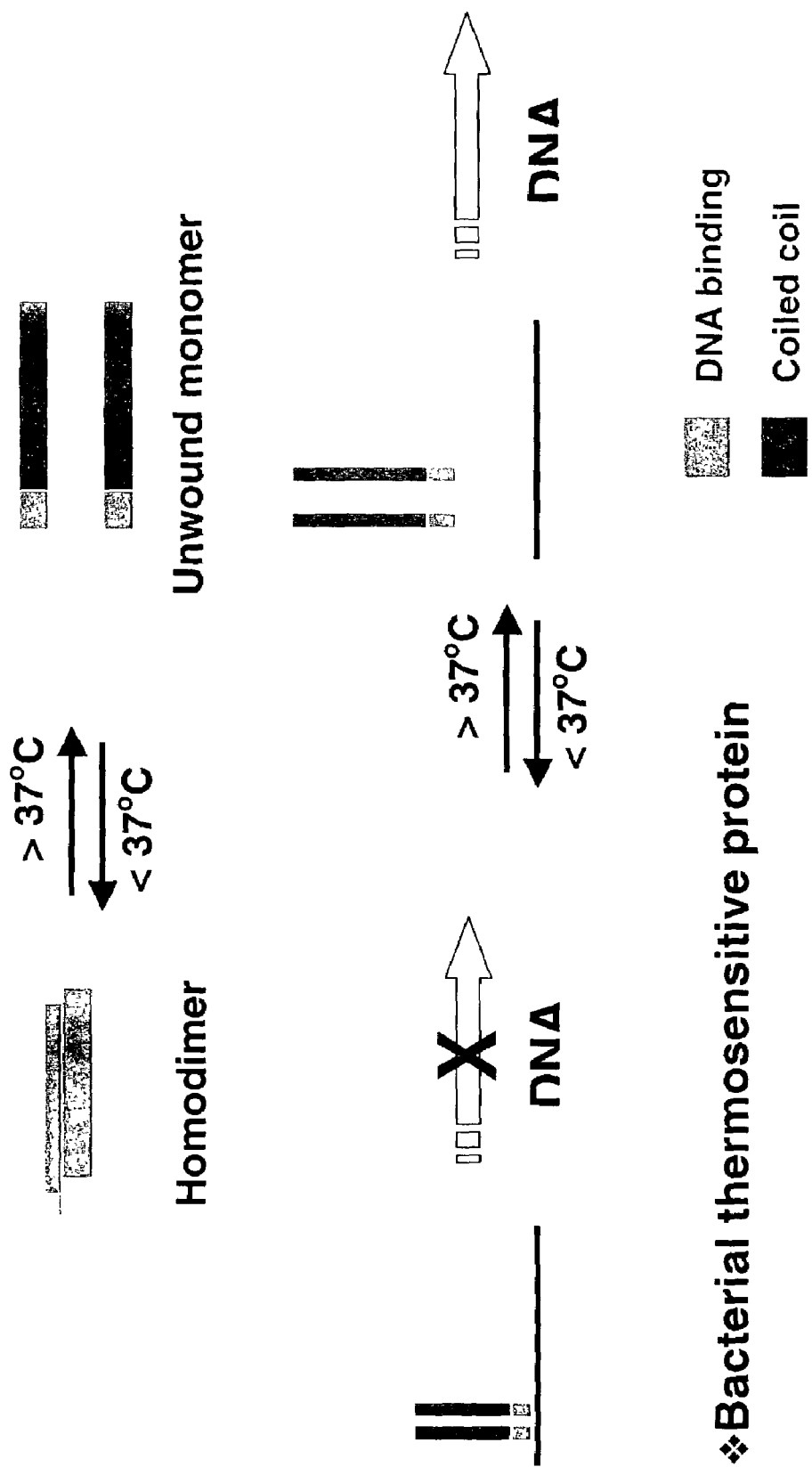
FIG. 2 is a schematic view of the conformational changes of the helical coiled-coil TlpA protein in accordance with the present invention.

The TlpA protein, along with its active fragments or derivatives, is a helical protein which forms a dimer at room temperature apparently via a coiled-coil helical interaction as shown schematically in FIG. 2. As has been noted by Koski et al., J. Biol. Chem. 267:12258–12265 (1992), incorporated herein by reference, it appears that the last 300 residues of the TlpA protein are helical, and thus this region appears to encompass the active thermal switch in accordance with the invention. As set forth further below, one such derivative from this region (TlpA8) has maintained the relevant switching portion of this protein and thus can be utilized in accordance with the present invention. Still other derivatives from this region which maintain the thermal switching ability of TlpA can also be utilized in accordance with the invention as described further below. At temperatures less than 37° C., the coiled-coil dimer associates with a specific regulatory sequence of the bacterial genome and prevents the transcription and subsequent expression of a series of proteins. In the host, or at temperatures greater than 37° C., the dimer dissociates from the DNA into monomers, allowing the genes to be transcribed to produce protein. Thus the natural function of TlpA is to operate as a thermal gene regulation switch. In accordance with the present invention, the TlpA protein or its active fragments or derivatives is thus utilized in an infrared detection device wherein the thermal switching affects the conductivity of a polymeric film containing the TlpA protein, and that conductivity is measured so as to determine the presence of the infrared radiation.

In accordance with the present invention, the inventors have developed an improved helical coiled coil protein with enhanced stability, solubility and tunability of the thermally sensitive proteins such as the TlpA protein. In this regard, it is possible to produce a TlpA protein fragment that contains at least one active portion of the TlpA protein, namely the section of the protein that undergoes the conformational changes described above. In accordance with the invention, one of these fragments has been designated TlpA8, whose protein sequence is shown in FIG. 8 and SEQ ID NO:1. This sequence corresponds to amino acids 257–299 of the full TlpA protein, whose sequence has been disclosed in prior references, including Hurme et al., *J. Biol. Chem.* 271: 12626–12631 (1996) and Koski et al., *J. Biol. Chem.* 267: 12258–12265 (1992), both incorporated herein by reference. The TlpA8 protein can also be constructed with a "His" tag, which will comprise one or more histidine residues added to the N-terminal end as an aid in purification. The present invention thus contemplates the isolated and/or purified TlpA8 protein to be utilized preferentially in the infrared detection devices of the invention.

As with the full TlpA protein, TlpA8 can be expressed recombinantly using conventional methods well known in this field and purified at large scale demonstrating the ability to produce sufficient quantity and quality of this material so as to support the commercial development of useful products. In accordance with the present invention, TlpA8 can be integrated into signal transduction means such as electrically conductive films as set forth in detail below which can meet the theoretical limit of 50 mK in sensitivity for semiconductor based infrared detectors operating at room temperature, and which possibly can be used in detectors operating with 3 mK in sensitivity, thus improving upon the sensitivity of detectors currently on the market In accordance with the present invention, two basic approaches may be utilized in creating signal transduction systems which can incorporate the helical coiled coil proteins such as heat sensing TlpA proteins of the present invention. The first such successfully developed system comprises thin films incorporated with the protein on which diffraction gratings can be created using precision lasers and similar newly developed technology. Examples of the production of such diffraction gratings are disclosed in Brott et al. (4) and Naik et al. (5), and these references are incorporated herein as if set forth in full. In addition, two-photon-induced photopolymerization may be used to create holographic patterns and other devices useful in three dimensional optical storage, such as described in Kirkpatrick et al. (6), and in pending U.S. patent application Ser. No. 09/657,169, filed Sep. 7, 2000, incorporated herein by reference, and these devices using optical signal transduction may also be utilized as substrates in the infrared detection systems of the present invention. It is also possible that holographic patterning can be used in accordance with the invention to form Fresnel lenses providing an alternate possibly more compact optical path to integrate the films into the electronic devices of the invention.

In the preferred embodiment of the invention, an infrared sensing device is provided which comprises an electrically conductive polymeric film which has the helical coiled coil proteins such as the thermally-sensing TlpA protein as described above incorporated therein, and this film is itself deposited onto an electrically conductive medium such as electrodes or a commercially available electric chip. In the preferred apparatus, variations in temperature are thus recorded by measuring the changes in conductivity or resistance of the polymer film as caused by the thermally-sensitive conformational changes of the coiled-coil protein in accordance with the invention. In the preferred embodiment, the electrically conductive polymer film will thus comprise a suitable polymer, either an electrically conductive polymer, and/or a polymeric material that has been doped with an electrically conductive particle, such as carbon black, and the thermosensitive protein such as TlpA in accordance with the invention as described above. In addition, optional surfactants and plasticizers may be added as necessary when so desired. Since the modulation of the oligomerization of carbon black is accomplished through the addition of protein, the protein of the invention is serving as a novel plasticizer. Finally, the electrically-conductive, thermal-sensing protein containing film will be connected through suitable electrical means such as electrodes or electrical chips, and suitable signal transduction means, to a suitable means such as a multimeter and/or a computer, so that the change in electrical conductivity and/or resistance can be measured and translated so as to detect the presence of infrared radiation in the target area of the detection device in accordance with the invention. In the preferred embodiment, the electrical properties of the film or gel can be read out using standard electrical readout equipment such as a multimeter, and the signal can also be translated by means of a computer so as to provide a readout that can be readily understood by the user of the device. This sensing concept may be applied using a single detection element, or can even be used in an array format, such as shown and described below. Such arrays based on integrated circuits which read out suspended bridge thermal sensing elements, can be fabricated from existing inexpensive components to form imaging systems for cameras, night vision equipment, etc.

In the preferred embodiment, the polymer used in the conductive polymer film which contains the thermally sensitive protein in accordance with the invention can be any suitable polymer that dissolves in a solvent miscible with the solvent used to dissolve the protein, and that the solvent does not adversely affect the functionality of the protein. Examples of useful solvents include but are not limited to dimethyl sulfoxide, acetonitrile and water, although numerous other solvents as would be contemplated by one of ordinary skill in this art may also be used. In accordance with the invention, a number of suitable polymers can be used to form the electrically conductive film in accordance with the invention, including polymers which have their own conductivity, or polymers into which a conductive material such as carbon black may be added. Such a suitable conductive carbon-containing polymer is disclosed, for example, in U.S. Pat. No. 6,290,911, incorporated herein by reference. Additional examples of suitable polymers include poly(ethylene oxide), poly(ethylene-co-vinyl alcohol), poly (vinyl acetate), gelatin, acacia, or poly(vinyl alcohol). Although not required for suitable functioning of the film in the infrared devices of the invention, it may be desired in some applications for the polymer to have functional groups for cross-linking. Accordingly, the polymers used in the conductive films of the invention may also have cross-linking, and thus cross-linking can be achieved through a number of suitable means, including chemically, photo-chemically, by gamma irradiation, or simply through strong hydrogen bonding across side groups of the polymer.

As indicated above, since it is desired to create a measurable resistance across the polymer film so as to translate the action of the conformational thermal sensing protein into an electrical signal, it is preferred that the polymeric film be constructed so that an electrically conductive material is incorporated into the matrix. In addition to the use of carbon black as described above, other suitable examples of the conductive particles useful in the invention include conductive silver flakes, gold particles, and metal coated ceramics. The amount of conductive material should preferably be in the percolation threshold range of the polymer matrix system so that even slight changes in conductive particle distances result in large changes of resistance.

As indicated above, the electrically conductive films of the invention include a thermally-sensing helical coiled-coil protein, and this protein is preferably used by dissolution in a solvent that will not inhibit the functionality of the protein. Additionally, if the solvent used is water, it is desirable that distilled water be used and not a buffered solution. Further considerations in the conductive polymeric matrix of the invention include the preferred requirement that the glass transition ($T_g$) of the matrix be lower than the operating temperature of the device. If the $T_g$ of the polymer host is above the operating temperature, it can be lowered through the use of plasticizers or modulated with any suitable means of active temperature control. Examples of suitable plasticizers include poly(ethylene glycol), glycerol or propylene glycol.

Additionally, it is preferred that the electronically conductive particles be homogeneously dispersed in the polymer matrix. When carbon black is used, a nonionic surfactant may be used to stabilize the dispersion of the conductive particles. A typical example of a surfactant is polyethylene (10) isooctylcyclohexyl ether, commercially sold as Triton X-100.

In general, the infrared detection devices of the invention can be constructed in a variety of suitable ways, as can the conductive film of the invention which contains the thermally sensitive coiled-coil protein such as the TlpA protein. In one suitable embodiment, the conductive film is obtained by dissolving a suitable polymer, such as poly(vinyl alcohol) in distilled water, and then heating and stirring for several hours at a suitable temperature (e.g., about 90–100° C.). In a separate flask, a suitable amount of carbon black (e.g., Vulcan XC-72, Cabot) is suspended in water and a suitable surfactant (e.g., Triton X-100) is added. Next, the carbon black and surfactant may be added to the polymer, e.g., by placing the vial in a water bath sonicator for 10 minutes, and then adding the contents to the polymer solution, and enough heat is generally supplied to evaporate the total water content to a suitable amount, e.g., 25 ml. Next, an optional plasticizing ingredient such as glycerol may be added to the polymer matrix, which is again stirred for an additional period under heat. Finally, the conductive polymeric matrix of the invention is obtained by removing the matrix from the heat source and allowed to cool to room temperature.

In the next step of preparing the thermally-sensitive conductive polymeric film of the invention, the polymer matrix such as obtained above is weighed out into a vial, and a suitable amount of the thermosensitive protein solution (e.g., in water) is added and mixed until homogeneous. A suitable wet film layer of this protein polymer mixture is then allowed to form, and may also be deposited onto an appropriate electrically conductive material, such as an electrode, and allowed to dry overnight to produce the completed thermal detector. Still further, it is also possible to deposit the protein polymer mixture containing the thermally sensitive protein of the invention onto other suitable devices which can be used to receive and translate optical signals, such as the nanopatterned peptide/silica hybrid structure such as disclosed in Brott et al., Nature 413: 291–293 (2001), incorporated herein by reference. In other embodiments, the polymeric film or gel composite with protein and an amorphous silicon chip for use as an active element in a detector system.

In one preferred embodiment of the invention, the thermal detector as obtained above may be utilized as a sensor array in imaging systems in which multiple detectors are utilized in one device, e.g., an integrated circuit which reads out suspended bridge thermal sensing elements. In the preferred embodiment, this receiving means can comprise a two-probe multimeter which is coupled to the thermal detector, and a computer which receives the output from the multimeter. In the preferred embodiment, the computer can graph the resistance of the detector as a function of time, so that fluctuations in temperature can be monitored in real time or recorded for subsequent review of the detection pattern. Suitable devices in accordance with the invention may be utilized to detect infrared radiation from a number of sources, and in a flashlight test performed in using a prototype of the present invention, the prototype clearly detected the infrared radiation from a small battery operated flashlight approximately 20 feet away. In this manner, a highly sensitive infrared detector may be formed which will be useful in a wide variety of applications such as described above. In addition, the conductive films of the invention may also be used in other devices and applications, such as uses in newly developed electronics manufacturing processes involving silk-screening.

Figure 3:
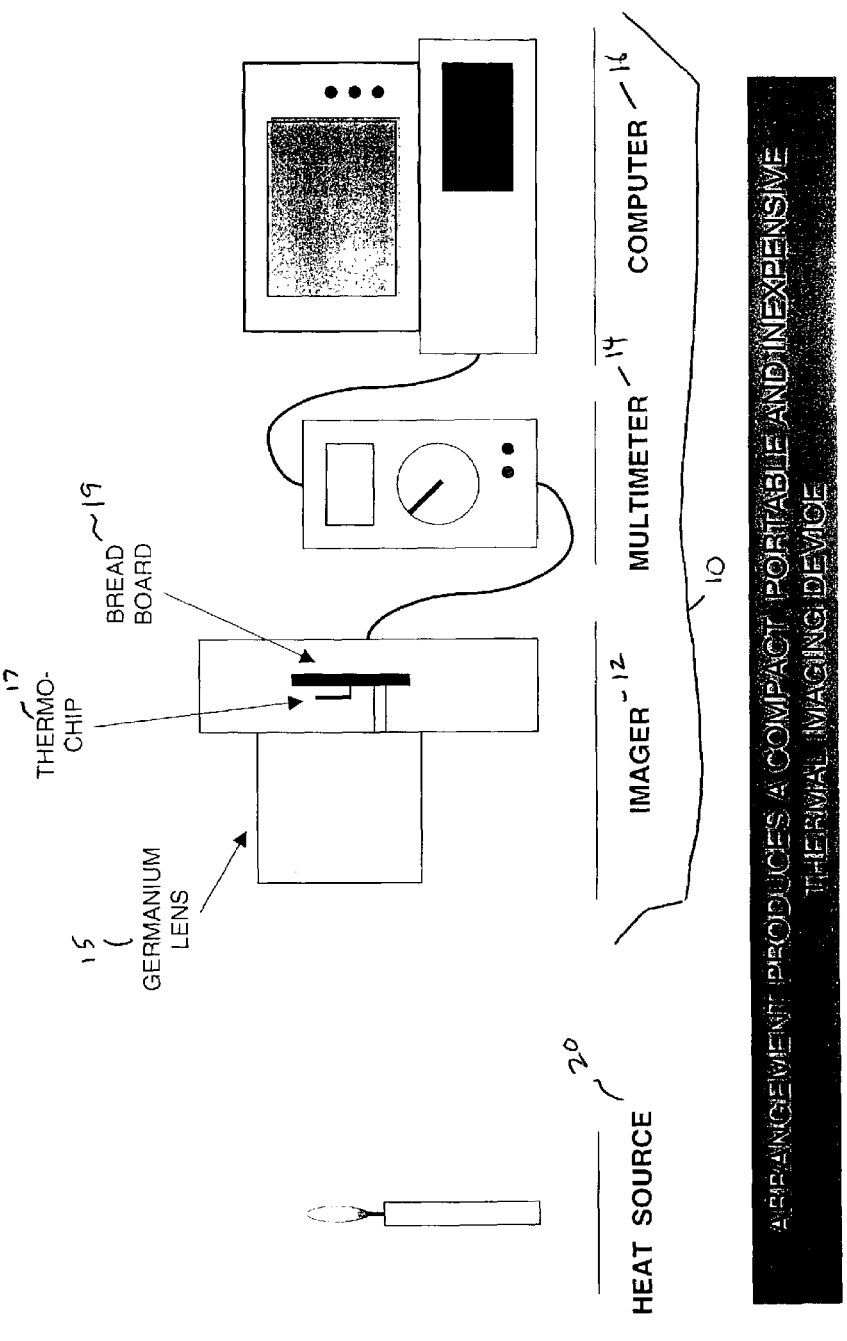
FIG. 3 is a schematic view of an infrared detection system in accordance with the present invention.
Figure 4:
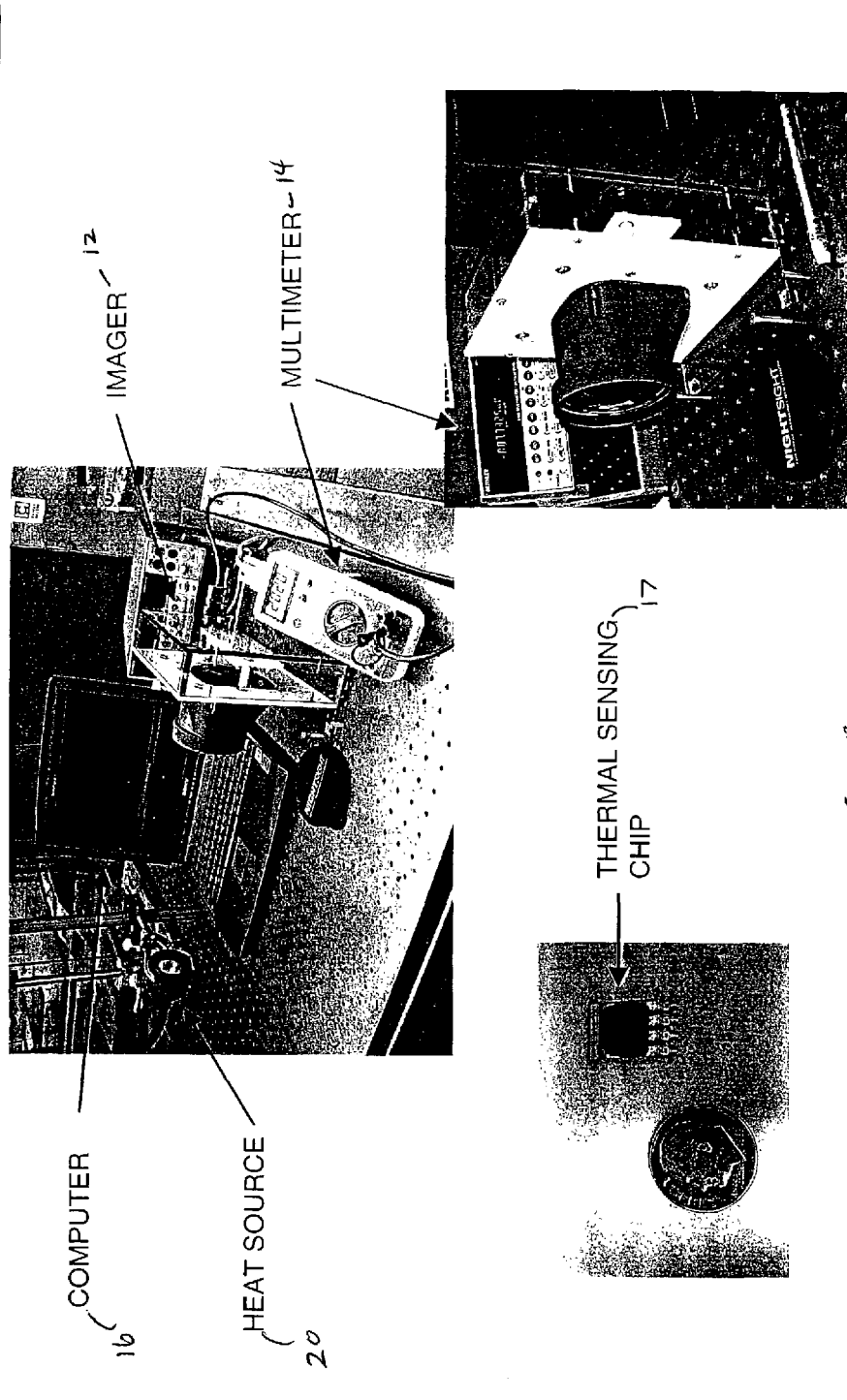
FIG. 4 is a photographic view of an infrared detection system in accordance with the present invention.

A summary of the elements of the preferred apparatus of the invention is shown in the schematic drawing FIG. 3. As shown in that figure, apparatus 10 is generally on the right side of the figure and is broken down into three general units, namely the imager 12 wherein the infrared radiation is received, focused and detected by the detector or detector array of the invention, the multimeter 14 which obtains a standard electrical readout from the imager, and the computer 16 which in this case can be utilized to interpret the electrical signal from the multimeter and present a suitable readout, either through digital, graphic or visual means, so that a user of the device can determine that infrared radiation has been detected from heat source 20. As shown in FIG. 3, the imager 12 of the invention can be constructed with a lens 15, such as a germanium lens as shown in the drawing, which can focus radiation from the heat source 20 onto the thermochip 17 which is comprised of the conductive polymeric matrix of the invention and includes a thermally sensitive coiled-coil protein as described above. The imager 12 also includes a "breadboard" 19 or electrode-type device, such as a standard commercially available electric chip which will transmit the electrical signal, i.e., the change in conductance or resistance caused by infrared radiation on the thermally-sensing protein in the conductive matrix as described above. This "breadboard" 19 is thus capable of transmitting a signal to a suitable electrical reading device such as multimeter 14, which then transmits the signal to a suitable analytical device such as a computer which will determine that infrared radiation has been detected based on the electrical signal. Actual versions of the elements of the present invention, including imager 12, multimeter 14, computer 16, thermal sensing chip 17, along with the heat source 20, are shown in FIG. 4.

Figure 5:
FIG. 5 is a photographic view of the sensing elements and printouts in accordance with the present invention.
Figure 5:
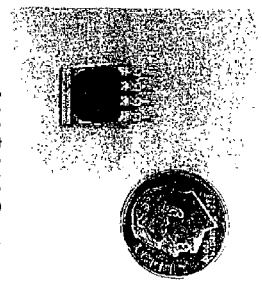
Figure 5:
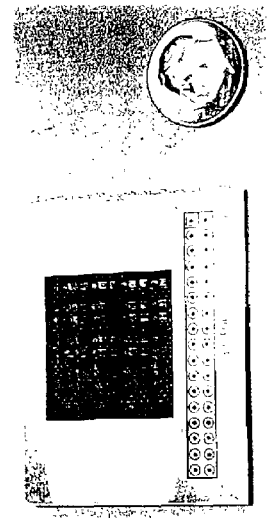
Figure 5:
Figure 5:
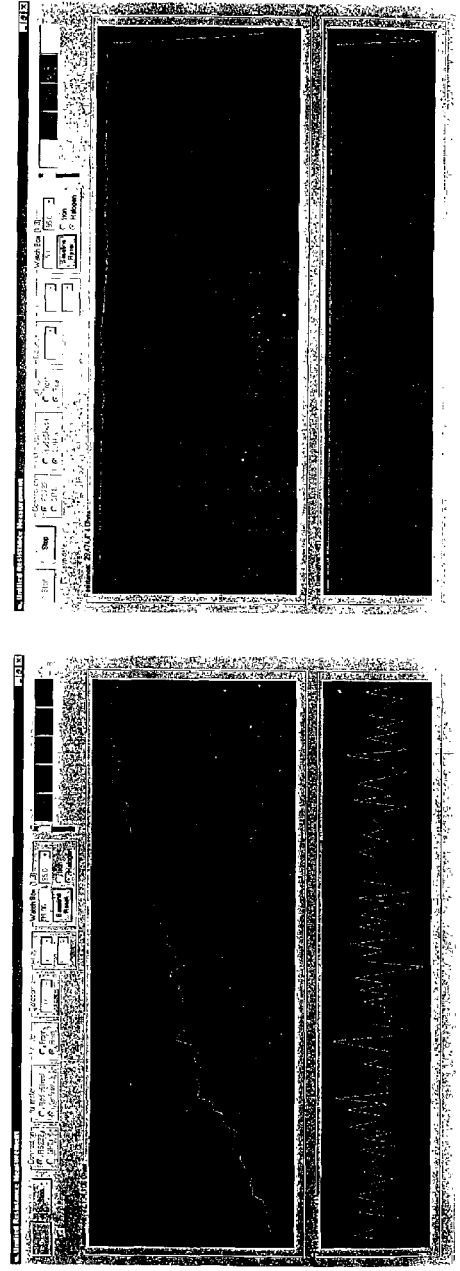

As indicated above, the thermal sensing chip 17, including the thermal sensing protein incorporated into the conductive polymer matrix, can be used alone or in a broad array of similar detectors. In these embodiments, as shown in FIG. 5, the thermal chip 17 can constitute a single element (left side), or in any number of suitable arrays wherein a plurality of detectors are used, including an array in a 1×7 pattern (FIG. 5, middle) and an array wherein a pattern of 4×4 sensing chips (right side) are used. Even further, other arrays such as 8×8, etc. may also be used. As one skilled in the art would recognize, the particular array that will be used will depend on the nature of the source to be detected and the nature or type of device that is being used for any particular application. As would be readily understood by one skilled in this art, the more detector chips that are utilized in an array, the more precise the detection of IR will become. At the same time, greater arrays of chips will often necessitate an increase in the power and scope of the analytical device, i.e., a computer with greater memory may be required in those applications having a broad array of detecting chips.

Figure 6:
FIG. 6 is a schematic view of the effect of the thermal sensing proteins of the invention on the conductivity of the polymer matrix of the present invention.
Figure 6:
Figure 6:
Figure 6:
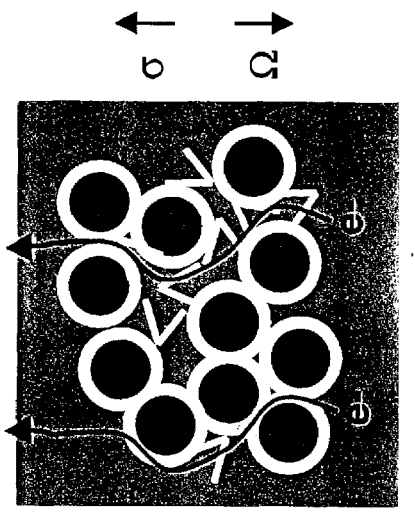
Figure 6:
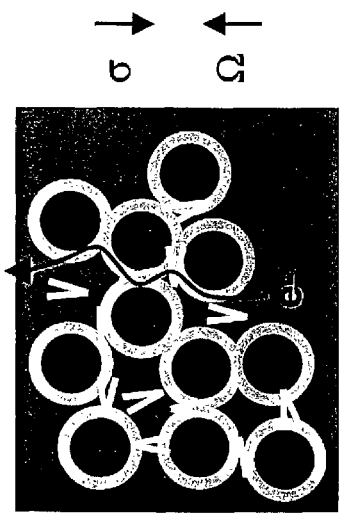

The general functioning of the thermal proteins of the present invention and their effect on the conductive film is shown in the schematic drawing of FIG. 6. As shown in this drawing, at low temperatures (left side), the polymer and thermal biomolecule tightly bind the conductive material (in this case, carbon black) in place. However, at higher temperatures (right side), the polymer and biomolecule expand, thereby allowing the conductive carbon black to rearrange and agglomerate, and as a result, the conductivity increases. It is this change in conductivity or resistance in the conductive polymer matrix of the invention which allows for the device to be used as a highly sensitive infrared detector as described above.

It is also the case that peptides or proteins are provided in accordance with the invention that contain an α-helical Coiled-coil (CC) structural motif, i.e., proteins or peptides which contain the heptapeptide repeating motif a-b-c-d-e-f-g with preferentially apolar or hydrophobic amino acids at positions 'a' and 'd' (Pauling, L. and Corey, R. B. 1953 Nature 171, 59–61), and these peptides or proteins can also be useful in the invention. With regard to these peptides and proteins, residues 'a' and 'd' of the "a-b-c-d-e-f-g" repeating motif form a hydrophobic backbone structure which drives and stabilizes the coiled-coil interactions between pairs of alpha helices. CC proteins are ubiquitous in nature and include collagen, myosin, TlpA, and many others. It would then be understood that CC proteins may have their respective sensitivity and wavelength response altered by the direct manipulation of residues 'a' and 'd' involved in forming the superhelical coil. Residues substituted at 'a' and 'd' which thermally stabilize the CC motif to higher temperature will decrease sensitivity and shift spectral response to shorter wavelengths. Conversely, residues substituted at 'a' and 'd' which destabilize the superhelical coil to increasing temperature will increase sensitivity and shift spectral response to longer wavelengths. It would also be understood that by decreasing the length of any CC protein at some point will destabilize the oligomeric superhelical interaction (increase sensitivity and shift spectral response to longer wavelengths) conversely increasing the length of the CC structure will decrease sensitivity and shift spectral response to shorter wavelengths.

In accordance with another aspect of the present invention, the substrate of the invention may comprise a hybrid organic/inorganic ordered nanostructure of silica spheres obtained through the incorporation of a polycationic peptide (such as derived from the *C. fusiformis* silaffin-1 protein) into a polymer hologram created by two-photon-induced photopolymerization. In this structure, such as disclosed in Broft et al., *Nature* 413, 291–293, (2001), incorporated by reference, the thermally sensing coiled-coil proteins of the invention may be incorporated and utilized in highly sensitive infrared detection devices.

In accordance with the present invention, the nanostructures of the invention may be prepared using diatoms to form intricate silica ordered nanostructures that comprise silica spheres obtained through the incorporation of a polycationic peptide (derived from the *C. fusiformis* silaffin-1 protein) into a polymer hologram created by two-photon-induced photopolymerization. When these peptide nanopatterned holographic structures are exposed to a silicic acid, an ordered array of silica nanospheres is deposited onto the clear polymer substrate. These structures exhibit a nearly fifty-fold increase in diffraction efficiency over a comparable polymer hologram without silica. This approach, combining the ease of processability of an organic polymer with the improved mechanical and optical properties of an inorganic material, will thus be useful in the present infrared detection devices disclosed above, as well as in other photonic devices.

A holographic two-photon-induced photopolymerization (H-TPIP) process as described in Kirkpatrick, S. M. et al., *Appl. Phys. A* 69, 461–464 (1999), incorporated herein by reference, may be utilized to prepare the ordered silica holograms of the present invention which can incorporate the thermally-sensing coiled-coil proteins described above. Unlike conventional holograms formed through the use of ultraviolet lasers, holograms created through the two-photon process use an ultrafast infrared laser. Because infrared wavelengths typically do not alter the functionality of biological compounds, monomer formulations containing peptides can be polymerized without affecting the biological activity. We incorporated a peptide that has recently been shown to be responsible for biosilification into a formulation to be cured by a holographic two-photon-induced photopolymerization with the expectation that the peptide would be segregated into regions of low crosslinking density. The approach of using ultraviolet lasers to phase separate small liquid crystal molecules in a polymer-based hologram has been used extensively and this technique is also applicable to the H-TPIP process. As predicted by the inventors, exposing the peptide-containing structure to a liquid silane causes silica to form in the holographic nanopattern and this hybrid organic/inorganic device has a higher degree of order leading to a superior device compared to randomly ordered monolayers of silica on indium-tin oxide (ITO) coated glass.

A short 19-amino-acid R5 peptide unit (SSKKSGSYSG-SKGSKRRIL) (SEQ ID NO:2) of the silaffin-1 precursor polypeptide from C. fusiformis can be used to catalyze the formation of silica nanospheres within minutes when added to silicic acid to neutral pH and ambient temperature. A chemically synthesized R5 peptide that lacks a post-translational modification of its lysine residues was used in the present work. The post-translational modification of lysine residues is required for silica formation under acidic pH conditions. However, in this case, the modification of the lysine residues was unnecessary. Consequently, the process started by incorporating this peptide (e.g., in water) into a monomer formulation. This formulation consisted of SR-9035, a trimethylolpropane triacrylate, and SR-399, a dipentaerythritol pentaacrylate obtained from Sartomer (which were used without the removal of inhibitor), along with triethanol amine and isopropyl thioxanthone; followed by heating the entire mixture to aid in dissolution. The triacrylate is preferred because of its high water miscibility which is due to its numerous ethylene glycol units, and the pentaacrylate was used to create a highly crosslinked system. The triethanol amine functions as a co-initiator and thioxanthone as the initiator. Typically, in a two-photon-initiated polymerization, a fluorescent chromophore is also required to absorb two photons of near-infrared laser light. The excited chromophore transfers its energy to the initiator which begins the polymerization process. However, we have found that the thioxanthone used in this formulation does not require highly colored chromophores, and consequently, extremely large curing depths and exceptionally clear and colorless polymers are produced.

A thin layer (e.g., about 178 μm) of the monomer/peptide formulation was deposited onto a clean glass slide, which was then placed in a miniature atmospheric chamber fitted with glass windows and flushed with nitrogen. The sample was cured in a two-beam transmission holographic arrangement using a 790-nm titanium-sapphire laser (90-fs pulse width with a repetition rate of 500 Hz) for 30 s. The intensity distribution of the volume hologram drives the local polymerization rate as a function of the local field intensity, which results in alternating areas of high and low crosslink density. Because certain areas of the sample cure more rapidly than others, the smaller molecules (namely water and peptide) phase separate from the areas of higher crosslink density and migrate into areas of lower density. This phenomenon has been observed in similar systems using liquid crystals as the small molecule. An alternative explanation of this phase separation could be that as the hydrophilic monomer is converted into a more hydrophobic polymer, the peptide is driven into the monomer-rich regions. As a result, peptide-rich domains are created in the polymer sample with the periodicity of the hologram. After the curing process, the sample was briefly rinsed with water to remove any uncured monomer. Atomic force microscopy (AFM) revealed that the hologram had a periodicity of 1.33 μm.

The silane precursor (1 M tetrahydroxysilane) was synthesized by dissolving tetramethyl orthosilicate (TMOS) in 1 mM HCl. This product was then added to a sodium phosphate-citrate buffer (pH 8) to produce a final concentration of 113 mM, and this dilute solution remains stable for over two hours, after which it slowly converts into a clear amorphous gel. Freshly prepared hydrolyzed silane was slowly applied to the hologram and allowed to react with the R5 peptide embedded in the hologram for 10 min. before being rinsed with water to remove any unreacted silane. A control hologram lacking the R5 peptide was also treated with the tetrahydroxysilane solution but did not exhibit any nanosphere formation. However, when a sample that included the peptide and was treated with the silane was analyzed by scanning electron microscope, it was revealed that silica spheres formed a regular two-dimensional array with the periodicity of the hologram. A study of the size distribution of the silica spheres reveals that the average nanosphere diameter is 452 nm (±81 nm). The silica content of the spheres was confirmed using electron dispersive spectroscopy (EDS). Additionally, analysis using the AFM indicated that the hologram had a periodicity of 1.60 μm with the silica spheres embedded in the troughs of the surface relief pattern. The difference in the spacing between the holograms treated with and without the tetrahydroxysilane solution can be explained by the fact that the control grating shrinks as it dries out owing to water evaporation, whereas the shrinkage in the hybrid hologram is inhibited owing to the added mechanical strength of the silica spheres, preventing the ridges of the hologram from moving closer together. Consequently, the untreated grating exhibited nearly 17% more shrinkage than the treated grating. Also, the silica spheres are the most prominent feature of the hologram and the troughs in the structure are actually the peaks of the polymer.

Finally, to test the improvement that this technique can impart to an optical device, the first-order diffraction efficiency of the treated hologram was compared to that of the untreated sample. These measurements were performed by transmitting a helium-neon laser through each sample and measuring the diffraction pattern in the far field. A measurement of the incident and transmitted power in the first-order diffraction spot showed a substantial increase in the diffraction efficiency of the grating with silica versus the grating without, as would be expected from the difference in index and shrinkage. The untreated grating exhibited a diffraction efficiency of approximately 0.02%, while the grating with the silica spheres showed an efficiency of approximately 0.95%. This large increase can be attributed to the fact that the spheres form an almost continuous line of silica along the valleys of the hologram, achieving a high fill factor.

We have thus shown that the incorporation of the peptide responsible for biosilification into a microfabricated structure using H-TPIP can result in an unusual composite organic/inorganic device that has significantly improved optical performance and superior mechanical properties compared to those of a corresponding polymeric device without silica. Although we have used a polymer/silica hybrid structure, this technique is universally applicable for any catalyst or binding agent that can be incorporated into a polymer. For example, as different catalysts are identified, a wide variety of unique hybrid structures are now possible with differing shapes and mechanical properties. Additionally, antibodies can be incorporated into the hologram and potentially used to optically identify specific antigens. Consequently, this technique allows a simple yet general and easily modifiable method for nanopatterning, and thus can provide a substrate for incorporation of the thermally sensitive proteins of the present invention.

It is thus submitted that the foregoing embodiments are only illustrative of the claimed invention and not limiting of the invention in any way, and alternative embodiments that would be obvious to one skilled in the art not specifically set forth above also fall within the scope of the claims.

REFERENCES

The following references as utilized in the detailed description above are incorporated by reference as if set forth in the above specification in full:
1. R. Hurme, K. D. Berndt, S. J. Normark, and M. Rhen, "A Proteinaceous Gene Regulatory Thermometer in *Salmonella*," *Cell* 90, 55–64 (1997).
2. A. L. Campbell, T. J. Bunning, M. O. Stone, D. Church, and M. S. Grace, "Surface Ultrastructure of Pit Organ, Spectacle, and Non Pit Organ Epidermis of Infrared Imaging Boid Snakes: A Scanning Probe and Scanning Electron Microscopy Study, *Journal of Structural Biology* 126, 105–120 (1999).
3. R. R. Naik, S. M. Kirkpatrick and M. O. Stone, "The Thermostability of an Alpha-helical Coiled-coil Protein and Its Potential use in Sensor Applications," *Biosensors & Bioelectronics*, 16, 1051–1057 (2001).
4. L. L. Brott, R. R. Naik, D. J. Pikas, S. M. Kirkpatric, D. W. Tomlin, P. W. Whitlock, S. J. Clarson, and M. O. Stone, "Ultrafast Holographic Nanopatterning of Biocatalytically Formed Silica," *Nature* 413, 291–293, (2001).
5. R. R. Naik, L. L. Brott, S. M. Kirkpatrick and M. O. Stone, "Functional Biomimetic Optical Devices," SPIE meeting in Australia December 17–19 (2001).
6. S. M. Kirkpatrick et al., "Holographic Recording Using Two-photon-induced Photopolymerization", *App. Phys. A.*, 69, 461–464 (1999).

The following examples are presented as illustrative of the present invention or methods of carrying out the invention, and are not restrictive or limiting of the scope of the invention in any manner.

EXAMPLES

Example 1

Preparation of a Sensing Device in Accordance with the Invention

Figure 7:
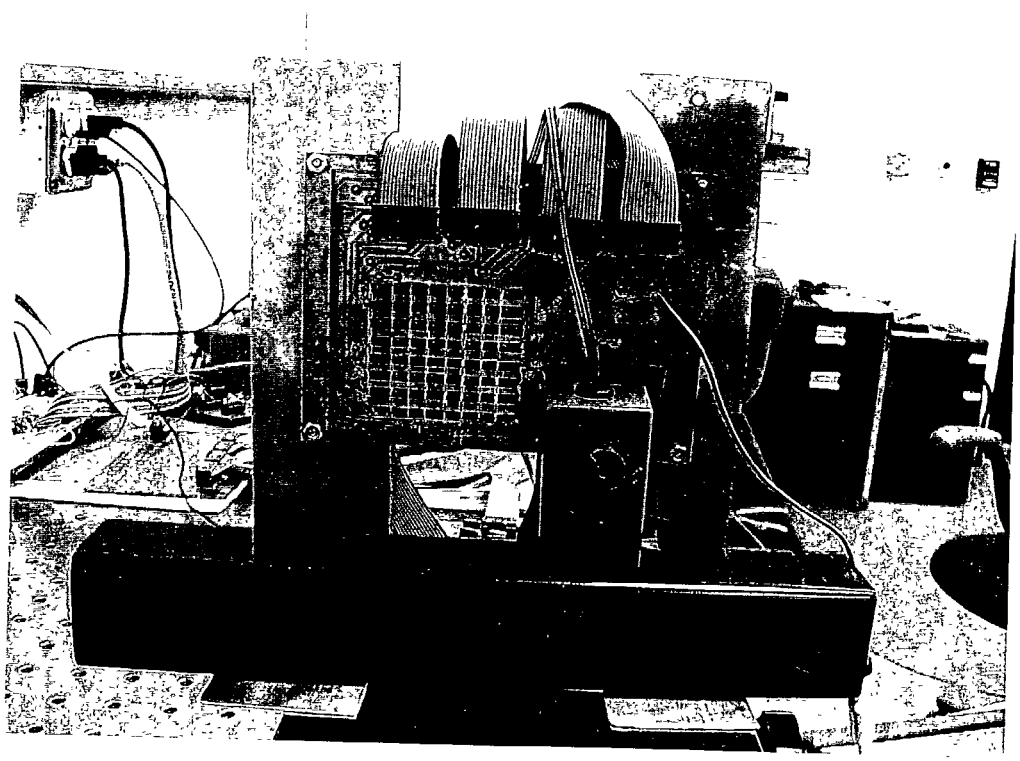
FIG. 7 is a photographic view of a prototype of an infrared detecting device of the invention including an 8×8 imaging array.

A prototype of a device in accordance with the present invention, as shown in FIG. 7, was prepared as follows: Poly(vinyl alcohol) (3.750 g, 98–99% hydrolyzed, average MW=85,000–146,000, Aldrich) is dissolved in distilled water (25 ml) through heating to 96° C. and stirring for three hours. In a separate flask, 0.563 g of carbon black (Vulcan XC-72, Cabot) is suspended in water (15 ml) and surfactant (21.0 µl, Triton X-100) by placing the vial in a water bath sonicator for 10 minutes and then added to the polymer solution and enough heat is supplied to evaporate the total water content to 25 ml. Glycerol (1.419 g Aldrich) is then added to the polymer matrix and stirred an additional 15 minutes. The polymer matrix is removed from the heat source and allowed to cool to room temperature.

The polymer matrix (0.666 g) is weighed into a vial and a thermosensitive protein solution (335 µl of 3 µg/µl TlpA in water) is added and mixed until homogeneous. A 254 µm wet layer if this protein polymer mixture is deposited onto two electrodes and allowed to dry overnight to produce the completed thermal detector.

A two-probe multi-meter is then coupled to the detector with its output fed into a computer. By graphing the resistance of the chip as a function of time, fluctuations in temperature can be monitored. In a flashlight test performed in a laboratory, the alpha prototype (8×8 sensing array) clearly detected and imaged the infrared radiation from a small battery operated flashlight approximately 20 feet across the laboratory. In a further test, a hand waved across the front of the detector clearly detected and crudely imaged the infrared radiation.

Performance Specifications of Alpha Prototype

The performance specifications of the alpha prototype in accordance with the invention are as follows:

Spectral Response: 3 to 5 Microns

Thermal Sensitivity: Approximately 50 mK

Response Time: 100 milliseconds (currently limited by electronics of prototype)

Operating Range: −16° C. to 65° C. (limited by glass phase transition temperature, $T_g$)

Dynamic Range: 15% Signal Change/° K

Optics & Readout: Standard

Example 2

Isolation and Testing of the TlpA Protein

Overview

Coiled-coil proteins are assemblies of two to four α-helices that pack together in a parallel or anti-parallel fashion. Coiled-coil structure can confer a variety of functional capabilities, which include enabling proteins such as myosin to function in the contractile apparatus of muscle and non-muscle cells. The TlpA protein encoded by the virulence plasmid of *Salmonella* is an α-helical protein that forms an elongated coiled-coil homodimer. A number of studies have clearly established the role of TlpA as a temperature-sensing gene regulator, however the potential use of a TlpA in a thermo-sensor application outside of the organism has not previously been done. In the following example, we demonstrate that TlpA has several characteristics that are common with α-helical coiled-coils and its thermal folding and unfolding is reversible and rapid. TlpA is extremely sensitive to changes in temperature. We also have compared the heat-stability of TlpA with other structurally similar proteins. Using a folding reporter, in which TlpA is expressed as a C-terminal fusion with green fluorescent protein (GFP), we were able to use fluorescence as an indicator of folding and unfolding of the fusion protein. Our results on the rapid conformational changes inherent in TlpA support the previous findings and we present here preliminary data on the use of a GFP-TlpA fusion protein as temperature sensor.

Introduction

The α-helical coiled-coil motif was first described in 1953 as the main structural element of a large class proteins, which include muscle proteins and transcription factors (Pauling and Corey, 1953; Lupas, 1996). Coiled-coils and helical bundles are two common α-helical motifs found in native proteins. Coiled-coil proteins are composed of two or more α-helices that are wound into a left-handed superhelix (Lupas, 1996). The α-helices are packed in a parallel or anti-parallel orientation with respect to one another. The formation of coiled coils are indicated by a heptad sequence repeat denoted [abcdefg], where positions a and d are occupied by hydrophobic residues, with polar residues at other positions. The coiled-coil structure in proteins confers a variety of functional capabilities: they form large rigid structures (keratins), molecular stalks (kinesins), levers (myosins) and can also act as scaffolds (tropomyosins) (Lupas, 1996).

The TlpA gene of Salmonella encodes an autoregulatory repressor protein that makes use of the coiled-coil motif to sense temperature changes and subsequently modulate transcription (Hurme et al., 1997). TlpA contains an N-terminal DNA-binding region and a large coiled-coil domain and has a tendency to form homodimers (Koski et al., 1992). It has been postulated that the molecular basis for thermosensing in TlpA is the dynamic coiled-coil to monomer structural transition that is directly coupled to differences in temperature. At temperatures below 37° C., TlpA assumes a coiled-coil formation that is capable of binding to sequence-specific DNA. Temperatures above 37° C. promote unfolding of TlpA, and these random coil monomers are unable to remain bound to DNA (Hurme et al., 1996). TlpA represents a novel class of molecules that has adapted the coiled-coil motif to function; coupling its transcriptional activity with protein folding, in response to temperature cues. The overproduction of TlpA in E. coli results in the formation of an ordered intermediate filament-like structure, which suggests that TlpA is able to aggregate into a higher order structure (Hurme et al., 1994).

Apart from TlpA, a number of native proteins as well as de novo designed coiled-coil peptides can undergo dramatic conformational changes in response to a variety of stimuli, such as pH, ionic strength and so forth. A number of papers have demonstrated the use of coiled-coil peptides in biotechnology and materials science research (Cho et al., 1998; Peak et al., 1998; Wang et al., 1999). For example, hybrid hydrogels, assembled from synthetic polymers and proteins, have potential in bioengineering applications such as cellular encapsulation and controlled reagent delivery systems. Hybrid hydrogels assembled from synthetic polymers and coiled-coil protein domains have been shown to be responsive to stimuli, but are hampered by slow recovery times (Wang et al., 1999). Although a number of design principles have been used in the de novo synthesis of peptides, it is quite clear that much can be learned from the folding interactions, stability and topology of native proteins. In this paper we demonstrate that the temperature-dependent reversible folding/unfolding of TlpA is rapid, and few proteins exhibit similar kinetics of folding/unfolding. In addition, using a GFP-TlpA fusion protein, we demonstrate the use of fluorescence as an indicator of structural transitions. The results presented here should allow us in the future to assemble hybrid hydrogels that display reversible and rapid temperature-dependent gel structural transitions, which would otherwise be difficult to achieve using hydrogels of synthetic polymers alone.

Materials and Methods

Bacterial Strains and Growth Conditions

Escherichia coli strains were grown in Luria Broth medium; for plasmid selection, ampicillin (100 mg/ml) was added (Sambrook et al., 1989). Recombinant proteins were expressed in E. coli BL21(DE3) strain (Novagen, Madison, Wis.).

Standard DNA Techniques

Standard procedures for plasmid isolations, restriction enzyme digestions, ligations, gel purification and transformation in bacteria were performed as described (Sambrook et al., 1989). Polymerase chain reaction (PCR) was performed using standard methods in a Perkin-Elmer Thermal Cycler. DNA sequence analysis was carried out on ABI Prism 310 Genetic Analyzer (Perkin-Elmer Applied Biosystems, Foster City Calif.).

Construction of Expression Vectors

TlpA and the coiled-coil domain (CC1) of Tar were amplified by conventional PCR from S. typhimurium and E. coli genomic DNA, respectively. Primers flanking the open reading frame of S. typhimurium TlpA gene and the coiled-coil domain of E. coli Tar gene were synthesized using published sequences (Genbank accession numbers: IM88208 and P07017). The amplification product was directly cloned into the TOPO vector (Invitrogen, Carlsbad, Calif.). The fragments were then digested out of the TOPO vector with appropriate restriction enzymes and cloned into the expression vector pET21 b (Novagen, Madison, Wis.). The GFP-TlpA expression plasmid was constructed by inserting in-frame the GFP (cycle 3 mutant) open reading frame upstream of TlpA in pET21 b. DNA sequence analysis was performed on GFP-TlpA, as well as all other expression plasmids.

Protein Expression and Purification pET21 b. DNA sequence analysis was performed on GFP-TlpA, as well as all other expression plasmids. The histidine-tagged recombinant proteins were expressed in E. coli BL21(DE3) after induction with 1 mM isopropyl R-thiogalactosidase (IPTG) at 30° C. for 3–4 hrs. The cell pellet was resuspended in Novagen binding buffer and sonicated with a microtip at the following settings: power level between 2–3 at 30% duty cycle for 10 secs. Bacterial lysates were pre-cleared at 25,000×g for 20 min, and applied directly onto a Ni-NTA metal affinity resin. The histidine tag permits the purification of the recombinant protein using standard procedures with a nickel-chelating resin. The purified protein was dialyzed extensively against 10 mM sodium phosphate buffer pH 7.0 and stored at −20° C. Protein purity was greater than 90% as determined by SDS-polyacrylamide gel electrophoresis (SDS-PAGE). Protein concentration was determined by the method of Bradford using a commercially available kit (Pierce, Rockford, Ill.).

Circular Dichorism Spectroscopy

CD spectra were measured in the range of 180 to 250 nm on a Jasco J-720 spectropolarimeter equipped with a temperature control unit. The ellipticity and wavelength were calibrated with a standard solution of L-10 camphosulfonic acid. The measurements were carried out at the indicated temperature using a 0.1 cm path length water jacketed quartz cuvette. Raw data were acquired at an interval of 1 nm and a bandwidth of 2 nm, and 3 consecutive scans were accumulated with a scan speed of 120 nm/min and averaged.

Fluorescence Spectroscopy

Fluorescence measurements of cell lysates prepared from equivalent number of cells, as measured by $OD_{500}$, were carried out on a Perkin-Elmer LS50B spectrofluorometer using 1 cm quartz cuvette. The excitation and emission wavelengths were set to 395 and 509 nm respectively, with a slit width set between 5 and 12 nm.

Results and Discussion

Circular Dichroism Analysis of Coiled-Coil Proteins

TlpA from *Salmonella* was expressed in *E. coli* and purified as described (see materials and methods). The circular dichroism (CD) spectrum of TlpA has the characteristic feature of an α-helical coiled-coil protein with negative ellipticity peaks at 222 and 208 nm. The evidence for the α-helical content (85%) and coiled-coil motif in TlpA has been previously well documented by Hurme et al., (1996). TlpA exhibits a significant structural transition as the temperature is increased from 25° C. to 55° C. Heating of TlpA to 55° C. results in the complete loss of α-helicity at 222 nm. This indicates that the folded coiled-coil protein undergoes a conformational change to an unfolded random coil.

The Tar gene which encodes for the aspartate receptor in *E. coli* is involved in thermotatic response, but the thermosensing mechanism is not well understood (Mizuno and Imae, 1984; Nara et al., 1996). We speculated that like TlpA, N terminal coiled-coil domain of Tar may serve a similar thermosensing function. We expressed and purified the coiled-coil domain (amino acid residues 34–190) as a histidine-tagged fusion protein in *E. coli*. The far-UV CD spectrum of purified CC1 shows a similar helical coiled-coil structure with negative ellipticity at 208 and 222 nm. CC1 is able to unfold to a random coil upon heating to 55° C. We believe that the structural transition of TlpA from a folded coiled-coil to an unfolded random coil conformation is a two-state equilibrium. A stepwise increase in temperature from 20° C. to 65° C. leads to the cooperative unfolding of TlpA as indicated by the loss of a-helicity at 222 nm. The presence of an isodichroic point at approximately 203 nm in the spectra obtained at different temperatures is indicative of a two-state α-helical to random coil transition (Hurme et al., 1997).

We took our analysis a step further by investigating whether the structural transition (α-helix to a random coil) induced by the thermal unfolding of TlpA or CC1 was reversible. Our research showed the reversibility of the structural transition (α-helix H random coil) as demonstrated by the recovery of the initial DE222 nm following cooling of the thermally unfolded protein. Previous research suggests that the unfolded TlpA is able to fold completely following heating to 55° C. (Hurme et al., 1997). We demonstrated that TlpA is able to completely recover following heating to 55° C. and 65° C. Additionally, the recovery was rapid (less than a minute) as observed by restoration of its α-helicity when cooled back to 10° C. In contrast, CC1 was unable to recover following cooling of the thermally unfolded protein to 10° C. Considering the physiological temperature range (37° C.–42° C.) at which bacteria are able to function, we observed very little recovery in the unfolding of CC1 following heating to temperatures above 42° C. The rapid recovery of TlpA following heating to 65° C. back to its native coiled-coil conformation is remarkable since structurally similar proteins either denature irreversibly at high temperatures or recover with much slower kinetics. The rapid recovery of TlpA following heating back to its native coiled-coil conformation is further supported by the fact that the loss of α-helicity during heating is reversible. As the temperature increases, a significant loss in the α-helical content of TlpA is observed. The α-helical structure is regained when the temperature is decreased. Our results showed that the kinetics of refolding was superimposable upon the kinetics of unfolding. These results in combination with those of Hurme et al., (1997) confirm that TlpA can serve as an active thermosensing device based on the properties of its coiled-coil domain. The rapid response of TlpA to temperature changes makes TlpA an ideal proteinaceous thermometer.

The irreversibility of the structural transition of CC1 suggests that the N-terminal coiled-coil domain may not serve as a thermosensor but only as a recognition site for aspartate. This is most likely the case since studies have implicated the cytoplasmic coiled-coil domain to be essential for thermosensing in vivo (Nishiyama et al., 1999). We are currently investigating whether the cytoplasmic coiled-coil domain of Tar can serve as a thermosensing device. In addition, using de novo protein design, we have been able to construct a small 16 amino acid coiled-coil peptide that exhibited some of the same thermodynamic properties of TlpA and the results of which will be published elsewhere.

GFP-TlpA Fusion Protein as Indicator of Structural Transitions

Green fluorescent protein (GFP) has become an important tool in cell biology and has been extensively used as a reporter molecule in biology (Misteli and Spector, 1997). De Angelis et al., (1998) demonstrated that tagging a protein with GFP can provide information about the protein's conformational state. When two GFP molecules are brought into close proximity, changes in the fluorescence intensity occurs when excited with 395 nm or 475 nm light. This phenomenon is called proximity imaging (PRIM). They demonstrated that homodimerization of a candidate protein, which is fused to GFP at either the amino- or carboxy-terminal, causes fluorescence quenching when excited at 395 nm. Waldo et al., (1999) used GFP as a fluorescent indicator of protein folding. It was shown that the fluorescence intensity of GFP is related to the productive folding of protein modules fused to GFP. Aggregation of the protein modules led to a decrease in the fluorescence intensity of the GFP chromophore. We decided to test whether fusing GFP to TlpA would act as fluorescent indicator of the structural transitions that occur in response to temperature changes. As mentioned earlier, TlpA is able to undergo structural transitions from a dimer to a monomer via its change from a coiled-coil to random coil conformation in response to thermal changes.

We constructed a GFP-TlpA folding reporter vector, wherein GFP is expressed as a N-terminal fusion with TlpA. The GFP-TlpA plasmid was transformed into and expressed in *E. coli* BL21(DE3). Induction with IPTG resulted in the appearance of fluorescent cells within 4 hours in liquid culture. Interestingly, longer incubation times lead to a decrease in fluorescence, which is most likely due to aggregation of the overproduced fusion protein (Naik and Stone, 2000). We postulated that at lower temperatures, formation of TlpA dimers would result in fluorescence quenching of the fused GFP modules. At higher temperatures, unfolding of the coiled-coil domains of TlpA leads to the dissociation of the dimers into monomers, which enhances the fluorescence of GFP. Our results showed that the fluorescent intensity of the GFP-TlpA fusion protein when excited at 395 nm increases by about 30% as the temperature is raised from 10° C. to 55° C. In contrast, when the temperature of GFP alone was increased from 10° C. to 55° C., we observed little change in the fluorescence intensity when excited at 395 nm. In fact, we observed that the fluorescence of GFP alone showed a decrease of approximately 10% at 55° C. The change in the fluorescence intensity of GFP-TlpA as a function of temperature is most likely due to the structural conformation of the downstream coiled-coil domain of TlpA. Further analysis of the effect of temperature on the fluorescence intensity of the GFP-TlpA fusion protein demonstrates that increasing the temperature from 10° C. to 37° C. leads to an intermediate increase in the fluorescent intensity when excited with 395 nm light. An additional increase in the fluorescent intensity is observed when the sample is heated further to 55° C. This process is reversible as shown by the decrease in the fluorescence intensity of the GFP-TlpA fusion protein as the temperature is lowered to 10° C. Although a single cycle is shown, the response was stable and reproducible over numerous cycles. In order to determine that fluorescent intensity of the GFP-TlpA fusion protein increases linearly with temperature, we plotted the fluorescence intensity versus temperature. The fluorescence intensity of the fusion protein increases linearly within the temperature range tested. These results clearly show that GFP functions as an indicator of the structural transitions in TlpA. The low fluorescence of the GFP-TlpA fusion protein at 10° C. is most likely due to the aggregation property of the TlpA dimers (Hurme et al., 1994). It is known that TlpA dimers are nonexchanging at room temperature or on ice, whereas they are dynamic chain exchanging structures at temperatures above 37° C. (Hurme et al., 1994). The gradual increase in fluorescence intensity of the GFP-TlpA fusion protein may be most arguably due to the dimer to monomer transition, since the addition of a reducing agent to the GFP-TlpA fusion protein sample causes the fluorescence to be unresponsive to temperature changes (data not shown). However, it is also likely that unfolding of the coiled-coil domain in response to an increase in temperature may indirectly affect the structure of the upstream GFP module. We are currently designing experiments that would differentiate between these two possibilities. Irrespective of the outcome of these experiments, it is quite clear from the results presented here that the fluorescence of GFP acts as an indicator of the structural transitions in TlpA in response to temperature.

CONCLUSIONS

Here we present our results on the thermostability of an α-helical coiled-coil bacterial thermosensor. TlpA exhibits a high degree of thermostability and an unusual reversible refolding ability. The kinetics of folding/unfolding of TlpA is rapid and different from that of other coiled-coil proteins. Increasing the temperature leads to the cooperative unfolding of the coiled-coil domain to an unfolded random coil. The unfolding of TlpA correlates quite well with increasing temperature, and the protein assumes a complete random coil conformation at temperatures higher than 55° C. Based on previous results on the use of GFP as a fluorescent indicator of protein folding (Waldo et al., 1999; De Angelis et al., 1998), we constructed a GFP-TlpA fusion protein that is responsive to temperature changes. We perceive the changes in the fluorescence of GFP to be a direct measure of changes in the structural conformation of TlpA. At low temperatures, GFP-TlpA forms dimers which results in fluorescence quenching. Increasing the temperature causes dissociation of dimers, in part due to the unfolding of the coiled-coil domain of TlpA, and an enhancement in fluorescence intensity.

Since signal transduction is perhaps the biggest obstacle to biosensor development, the TlpA proteins of the invention will be extremely useful in overcoming this problem. Biological signal transduction usually involves an extremely complicated sequence of molecular recognition and binding packaged in a specific set of steps. By utilizing the TlpA protein, we have isolated an initial sensing molecule i.e., the "trigger", and can thus use this protein in achieving an optical readout as a measure of the transduction process.

Previously, one weakness of protein-based biological sensors was the speed of response, especially in a thermal process because proteins almost always exhibit a prolonged unfolding-refolding cycle, i.e., several minutes, that is too slow for most sensing applications. However, the use of the TlpA protein in accordance with the invention overcomes these problems because of its unfolding/refolding cycle which is incredibly fast. It remains unclear as to exactly how quickly TlpA can respond to thermal stimuli, but the protein has responded faster than we can shift the temperature and produce thermal equilibrium. Albeit that the response time of the GFP-TlpA fusion protein was slower than that of TlpA alone, two different techniques (CD spectroscopy versus Fluorescence spectroscopy) were used in measuring responses to temperature changes.

In accordance with the invention, the TlpA protein can thus be incorporated into polymer hydrogels in order to exploit the thermodynamic properties of TlpA in a manner previously not obtained, and these hybrid hydrogels will be assembled from synthetic polymers and TlpA. The dissociation of the coiled-coil aggregates of TlpA through elevation of temperature cause dissolution of the gel network and a return to a more porous state. Such materials or hybrid hydrogels in accordance with the present invention thus have potential in a number of biosensor applications requiring controlled release of molecules embedded in the hydrogel.

REFERENCES

The following references as utilized in the Example above are incorporated by reference as if set forth in the above specification in full:

Chao, H., D. L. Bautista, J. Litowski, R. T. Irvin, and R. S. Hodges. 1998. Use of a heteromeric coiled-coil system for biosensor application and affinity purification. J. Chromatogr. B Biomed. Appl. 715:307–329.

De Angelis, D. A., G. Miesenbock, B. V. Zemelman, and J. E. Rothman. 1998. PRIM: Proximity imaging of green fluorescent protein-tagged polypeptides. Proc. Natl. Acad. Sci. USA. 95:12312–12316.

Hurme, R., K. D. Berndt, E. Namork, and M. Rhen. 1996. DNA binding exerted by a bacterial gene regulator with an extensive coiled-coil domain. J. Biol. Chem. 271: 12626–12631.

Hurme, R., K. D. Berndt, S. J. Normark, and M. Rhen. 1997. A proteinaceous gene regulatory thermometer in *Salmonella*. Cell. 90:55–64.

Hurme, R., E. Namork, E. Nurmiaho-Lassila, and M. Rhen. 1994. Intermediate filament-like network formed in vitro by a bacterial coiled-coil protein. J. Biol. Chem. 269: 10675–10682.

Koski, P., H. Saarilahti, S. Sukupolyi, S. Taira, P. Riikonen, K. Osterlund, R. Hurme, and M. Rhen. 1992. A new α-helical coiled-coil protein encoded by the *Salmonella typhimurium* virulence plasmid. J. Biol. Chem. 267:12258–12265.

Lupas, A. 1996. Coiled coils: new structures and functions. Trends Biochem. Sci. 21:375–382.

Misteli, T., and D. L. Spector. Applications of the green fluorescent protein in cell biology and biotechnology. Nat. Biotechnol. 15:961–964.

Mizuno, T., and Y. Imae. 1984. Conditional inversion of the thermoresponse in *Escherichia coli*. J. Bacteriol. 159:360–367.

Naik, R. R., and M. O. Stone 2000. The use of green fluorescent protein as an indicator in protein expression. In preparation. Nara, T., I. Kawagishi, S. Nishiyama, M. Homma, and Y. Imae. 1996. Modulation of the thermosensing profile of the *Escherichia coli* aspartate receptor Tar by covalent modification of the methyl-accepting site. J. Biol. Chem. 271:17932–17936.

Nishiyama, S., I. N. Maruyama, M. Homma, and I. Kawagishi. 1999. Inversion of the thermosensing property of the bacterial receptor Tar by mutations in the second transmembrane region. J. Mol. Biol. 286:1275–1284.

Pauling, L., and R. B. Corey. 1953. Compound helical configurations of polypeptide chains: structure of proteins of the x-keratin type. Nature. 171:59–61.

Petka, W. A., J. L. Harden, K. P. McGrath, D. Wirtz, and D. A. Tirrell. 1998. Reversible hydrogels from self-assembling artificial proteins. Science. 281:389–392.

Sambrook, J., E. F. Fritsch, and T. Maniatis. 1989. Molecular Cloning: A Laboratory Manual. Cold Spring Harbor Laboratory Press, Cold Spring Harbor, N.Y.

Waldo, G. S., B. M. Standish, J. Berendzen, and T. C. Terwilliger. 1999. Rapid protein-folding assay using green fluorescent protein. Nat. Biotechnol. 17:691–695.

Wang, C., R. J. Stewart, and J. Kopecek. 1999. Hybrid hydrogels assembled from synthetic polymers and coiled-coil protein domains. Nature. 397:417–420.

Example 3

Preparation of a Holographic Nanopattern of Biocatalytically Formed Silica for Use in the Present Invention In accordance with the present invention, a structure for use with the thermally sensing proteins of the present invention was developed from another form of nature: diatoms.

Diatoms are of interest to the materials research community because of their ability to create highly complex and intricate silica structures under physiological conditions: what these single-cell organisms accomplish so elegantly in nature requires extreme laboratory conditions to duplicate[1,2]-this is true for even the simplest of structures. Following the identification of polycationic peptides from the diatom *Cylindrotheca fusiformis*, simple silica nanospheres can now be synthesized in vitro from silanes at nearly neutral pH and at ambient temperatures and pressures[3,4]. Here we describe a method for creating a hybrid organic/inorganic ordered nanostructure of silica spheres through the incorporation of a polycationic peptide (derived from the *C. fusiformis* silaffin-1 protein) into a polymer hologram created by two-photon-induced photopolymerization. When these peptide nanopatterned holographic structures are exposed to a silicic acid, an ordered array of silica nanospheres is deposited onto the clear polymer substrate. These structures exhibit a nearly fifty-fold increase in diffraction efficiency over a comparable polymer hologram without silica. This approach, combining the ease of processability of an organic polymer with the improved mechanical and optical properties of an inorganic material, could be of practical use for the fabrication of photonic devices.

We have recently developed a holographic two-photon-induced photopolymerization (H-TPIP) process[5] and here we describe how this technique can be used to prepare nanopatterned structures that contain biological macromolecules such as the TlpA proteins of the present invention. Unlike conventional holograms formed through the use of ultraviolet lasers, holograms created through the two-photon process use an ultrafast infrared laser. Because infrared wavelengths typically do not alter the functionality of biological compounds, monomer formulations containing peptides can be polymerized without affecting the biological activity. We incorporated a peptide that has recently been shown to be responsible for biosilification into a formulation to be cured by a holographic two-photon-induced photopolymerization with the expectation that the peptide would be segregated into regions of low crosslinking density. The approach of using ultraviolet lasers to phase separate small liquid crystal molecules in a polymer-based hologram has been used extensively[6] and we hypothesized that this technique would also be applicable to the H-TPIP process. We predicted that exposing the peptide-containing structure to a liquid silane would cause silica to form in the holographic nanopattern and that this hybrid organic/inorganic device would have a higher degree of order leading to a superior device compared to randomly ordered monolayers of silica on indium-tin oxide (ITO) coated glass[7].

A short 19-amino-acid R5 peptide unit (SSKKSGSYSG-SKGSKRRIL) (SEQ ID NO:2) of the silaffin-1 precursor polypeptide from *C. fusiformis* is able to catalyze the formation of silica nanospheres within minutes when added to silicic acid to neutral pH and ambient temperature[3]. A chemically synthesized R5 peptide that lacks a post-translational modification of its lysine residues was used in the present work. The post-translational modification of lysine residues is required for silica formation under acidic pH conditions[3,8]. However, because our research was conducted under slightly basic conditions, the modification of the lysine residues was unnecessary. Consequently, work began by incorporating this peptide (0.8 mg in 16 µl of water) into a monomer formulation. This formulation consisted of 160 µl SR-9035, 0.022 g SR-399 (SR-9035 is a trimethylolpropane triacrylate and SR-399 is a dipentaerythritol pentaacrylate obtained from Sartomer which were used without the removal of inhibitor), 0.006 g triethanol amine and 0.005 g isopropyl thioxanthone; the entire mixture was heated for 15 min at 50° C. to aid in dissolution. The triacrylate was chosen for its high water miscibility which is due to its numerous ethylene glycol units, and the pentaacrylate was used to create a highly crosslinked system. The triethanol amine functions as a co-initiator and thioxanthone as the initiator. Typically, in a two-photon-initiated polymerization, a fluorescent chromophore is also required to absorb two photons of near-infrared laser light. The excited chromophore transfers its energy to the initiator which begins the polymerization process. However, we have found that the thioxanthone used in this formulation does not require highly colored chromophores, and consequently, extremely large curing depths and exceptionally clear and colorless polymers are produced[9,10].

A thin layer (178 μm) of the monomer/peptide formulation was deposited onto a clean glass slide, which was then placed in a miniature atmospheric chamber fitted with glass windows and flushed with nitrogen. The sample was cured in a two-beam transmission holographic arrangement using a 790-nm titanium-sapphire laser (90-fs pulse width with a repetition rate of 500 Hz) for 30 s. The intensity distribution of the volume hologram drives the local polymerization rate as a function of the local field intensity, which results in alternating areas of high and low crosslink density. Because certain areas of the sample cure more rapidly than others, the smaller molecules (namely water and peptide) phase separate from the areas of higher crosslink density and migrate into areas of lower density. This phenomenon has been observed in similar systems using liquid crystals as the small molecule. An alternative explanation of this phase separation could be that as the hydrophilic monomer is converted into a more hydrophobic polymer, the peptide is driven into the monomer-rich regions. As a result, peptide-rich domains are created in the polymer sample with the periodicity of the hologram. After the curing process, the sample was briefly rinsed with water to remove any uncured monomer. Atomic force microscopy (AFM) revealed that the hologram had a periodicity of 1.33 μm.

The silane precursor (1 M tetrahydroxysilane) was synthesized by dissolving tetramethyl orthosilicate (TMOS) in 1 mM HCl. This product was then added to a sodium phosphate-citrate buffer (pH 8) to produce a final concentration of 113 mM. We note that this dilute solution remains stable for over two hours, after which it slowly converts into a clear amorphous gel. Freshly prepared hydrolyzed silane was slowly applied to the hologram and allowed to react with the R5 peptide embedded in the hologram for 10 min. before being rinsed with water to remove any unreacted silane. A control hologram lacking the R5 peptide was also treated with the tetrahydroxysilane solution but did not exhibit any nanosphere formation. However, when a sample that included the peptide and was treated with the silane was analyzed by scanning electron microscope, it was revealed that silica spheres formed a regular two-dimensional array with the periodicity of the hologram. A study of the size distribution of the silica spheres reveals that the average nanosphere diameter is 452 nm (±81 nm). The silica content of the spheres was confirmed using electron dispersive spectroscopy (EDS). Additionally, analysis using the AFM indicated that the hologram had a periodicity of 1.60 μm with the silica spheres embedded in the troughs of the surface relief pattern. The difference in the spacing between the holograms treated with and without the tetrahydroxysilane solution can be explained by the fact that the control grating shrinks as it dries out owing to water evaporation, whereas the shrinkage in the hybrid hologram is inhibited owing to the added mechanical strength of the silica spheres, preventing the ridges of the hologram from moving closer together. Consequently, the untreated grating exhibited nearly 17% more shrinkage than the treated grating. Also, the silica spheres are the most prominent feature of the hologram and the troughs in the structure are actually the peaks of the polymer.

Finally, to test the improvement that this technique can impart to an optical device, the first-order diffraction efficiency of the treated hologram was compared to that of the untreated sample. These measurements were performed by transmitting a helium-neon laser through each sample and measuring the diffraction pattern in the far field. A measurement of the incident and transmitted power in the first-order diffraction spot showed a substantial increase in the diffraction efficiency of the grating with silica versus the grating without, as would be expected from the difference in index and shrinkage. The untreated grating exhibited a diffraction efficiency of approximately 0.02%, while the grating with the silica spheres showed an efficiency of approximately 0.95%. This large increase can be attributed to the fact that the spheres form an almost continuous line of silica along the valleys of the hologram, achieving a high fill factor.

We have thus shown that the incorporation of the peptide responsible for biosilification into a microfabricated structure using H-TPIP can result in an unusual composite organic/inorganic device that has significantly improved optical performance and superior mechanical properties compared to those of a corresponding polymeric device without silica. Although we have used a polymer/silica hybrid structure, this technique is universally applicable for any catalyst or binding agent that can be incorporated into a polymer. For example, as different catalysts are identified, a wide variety of unique hybrid structures are now possible with differing shapes and mechanical properties. Additionally, antibodies can be incorporated into the hologram and potentially used to optically identify specific antigens. Consequently, this technique allows a simple yet general and easily modifiable method for nanopatterning, and thus can provide a substrate for incorporation of the thermally sensitive TlpA proteins of the present invention.

REFERENCES

The following references as utilized in the Example above are incorporated by reference as if set forth in the above specification in full:

1. Parkinson, J. & Gordon, R. Beyond micromachining: the potential of diatoms. *Trends Biotechnol.* 17, 190–196 (1999).
2. Morse, D. E. Silicon biotechnology: harnessing biological silica production to construct new materials. *Trends Biotechnol.* 17, 230–232 (1999).
3. Kröger, N., Deutzmann, R. & Sumper, M. Polycationic peptides from diatom biosilica that direct silica nanosphere formation. *Science* 286, 1129–1132 (1999).
4. Cha, J. N., Stucky, G. D., Morse, D. E. & Deming, T. J. Biomimetic synthesis of ordered silica structures mediated by block copolypeptides. *Nature* 403, 289–292 (2000).
5. Kirkpatrick, S. M. et al. Holographic recording using two-photon-induced photopolymerization. *Appl. Phys. A* 69, 461–464 (1999).
6. Bunning, T. J. et al. The morphology and performance of holographic transmission gratings recorded in polymer dispersed liquid crystals. *Polymer* 36, 2699–2708 (1995).
7. Wang, C. et al. Two-dimensional ordered arrays of silica nanoparticles. *Chem. Mater.* 12, 3662–3666 (2000).
8. Kröger, N., Deutzmann, R. & Sumper, M. Silica-precipitating peptides from diatoms, the chemical structure of silaffin-1a from *Cylindrotheca fusiformis*. *J. Biol. Chem.* 276, 26066–26070 (2001).
9. Belfield, K. D. et al. Multiphoton-absorbing organic materials for microfabrication, emerging optical applications and non-destructive three-dimensional imaging. *J. Phys. Org. Chem.* 13, 837–849 (2000).
10. Brott, L. L. Naik, R. R., Kirkpatrick, S. M. Pikas, D. J. & Stone, M. O. Near-IR two-photon induced polymerizations using either benzophenone or thioxanthone-based photoinitiators. *Polymer Preprints* 42, 675–676 (2001).

What is claimed is:

1. An apparatus for sensing infrared radiation comprising an electrically conductive film or gel containing therein a naturally occurring or recombinant temperature-sensing helical coiled-coil protein which undergoes reversible conformational change in the range of −15° C. to 60° C., means for detecting changes in conductivity or resistance of the conductive film or gel caused by the effect of infrared radiation on the protein, and means to determine a presence of infrared radiation based on the changes in conductivity or resistance of the conductive film or gel wherein the protein is TlpA8.

2. An apparatus for sensing infrared radiation comprising an electrically conductive film or gel containing therein a naturally occurring or recombinant temperature sensing helical coiled-coil protein which undergoes reversible conformational change in the range of −15 degrees C. to 60 degrees C., means for detecting changes in conductivity or resistance of the conductive film or gel caused by the effect of infrared radiation on the protein, and means to determine a presence of infrared radiation based on the changes in conductivity or resistance of the conductive film or gel wherein the protein has the amino acid sequence of SEQ ID NO: 1.

3. An electrically conductive film or gel suitable for use in an infrared detection device comprising a conductive polymer matrix having incorporated therein a naturally occurring or recombinant temperature-sensing helical coiled-coil protein which has a reversible conformational change in the range of −15° C. to 60° C. wherein the protein is TlpA8.

4. An isolated recombinant protein consisting essentially of TlpA8.

5. An isolated recombinant protein consisting essentially of the amino acid sequence of SEQ ID NO: 1.

6. An isolated recombinant protein consisting essentially of TlpA8 and a His tag.

* * * * *

SEQUENCE LISTING

```
<160> NUMBER OF SEQ ID NOS: 2

<210> SEQ ID NO 1
<211> LENGTH: 43
<212> TYPE: PRT
<213> ORGANISM: Salmonella typhimurium

<400> SEQUENCE: 1

Thr Arg Glu Thr Leu Gln Gln Arg Leu Glu Gln Ala Ile Ala Asp Thr
1               5                   10                  15

Gln Ala Arg Ala Gly Glu Ile Ala Leu Glu Arg Asp Arg Val Ser Ser
            20                  25                  30

Leu Thr Ala Arg Leu Glu Ser Gln Glu Lys Ala
        35                  40

<210> SEQ ID NO 2
<211> LENGTH: 19
<212> TYPE: PRT
<213> ORGANISM: Cylindrotheca fusiformis

<400> SEQUENCE: 2

Ser Ser Lys Lys Ser Gly Ser Tyr Ser Gly Ser Lys Gly Ser Lys Arg
1               5                   10                  15

Arg Ile Leu
```